United States Patent
Hedberg et al.

(10) Patent No.: US 9,162,066 B2
(45) Date of Patent: Oct. 20, 2015

(54) METHOD AND SYSTEM FOR STIMULATING A HEART

(75) Inventors: Sven-Erik Hedberg, Kungsangen (SE); Nils Holmstrom, Jarfalla (SE); Karin Jarverud, Solna (SE)

(73) Assignee: ST. JUDE MEDICAL AB, Jarfalla (SE)

( * ) Notice: Subject to any disclaimer, the term of this patent is extended or adjusted under 35 U.S.C. 154(b) by 350 days.

(21) Appl. No.: 13/508,968

(22) PCT Filed: May 31, 2011

(86) PCT No.: PCT/EP2011/058982
§ 371 (c)(1),
(2), (4) Date: Aug. 8, 2012

(87) PCT Pub. No.: WO2012/163414
PCT Pub. Date: Dec. 6, 2012

(65) Prior Publication Data
US 2014/0257423 A1 Sep. 11, 2014

(51) Int. Cl.
*A61N 1/368* (2006.01)
*A61N 1/362* (2006.01)

(52) U.S. Cl.
CPC .............. *A61N 1/368* (2013.01); *A61N 1/3622* (2013.01); *A61N 1/3682* (2013.01); *A61N 1/3684* (2013.01)

(58) Field of Classification Search
CPC . A61N 1/3706; A61N 1/3702; A61N 1/3627; A61N 1/368; A61N 1/3684; A61N 1/37; A61N 1/3682; A61N 1/056; A61N 1/362; A61N 1/3622; A61N 1/3621; A61N 1/365; A61N 1/3937; A61N 1/3714; A61B 5/0452; A61B 5/7217

USPC .......................................................... 607/27
See application file for complete search history.

(56) References Cited

U.S. PATENT DOCUMENTS

| | | | |
|---|---|---|---|
| 4,484,586 | A | 11/1984 | McMickle et al. |
| 5,057,092 | A | 10/1991 | Webster et al. |
| 6,132,456 | A | 10/2000 | Sommer et al. |
| 6,381,500 | B1 | 4/2002 | Fischer, Sr. |
| 6,438,425 | B1 | 8/2002 | Miller et al. |
| 6,606,522 | B2 | 8/2003 | Schell |
| 7,590,446 | B1 | 9/2009 | Min et al. |

(Continued)

FOREIGN PATENT DOCUMENTS

| | | | |
|---|---|---|---|
| EP | 0602859 | A2 | 6/1994 |
| EP | 0602859 | A3 | 2/1995 |
| EP | 2229210 | B1 | 5/2011 |

OTHER PUBLICATIONS

Search Report—Parent Case—Intern'l Application No. PCT/EP2011/058982.

(Continued)

*Primary Examiner* — Christopher D Koharski
*Assistant Examiner* — Jeremiah Kimball

(57) ABSTRACT

A first ventricle is stimulated at a stimulation site, a point of time for arrival at the AV node for at least one depolarization wave resulting from the stimulation is estimated and a first activation time interval substantially corresponding to the time interval required for at least one depolarization wave to travel from the stimulation site in the first ventricle to the AV node is computed. A similar process is used to compute a second activation time interval for the other ventricle. Based on these activation time intervals and a difference between the intervals, a pacing therapy can be determined.

15 Claims, 9 Drawing Sheets

(56) References Cited

U.S. PATENT DOCUMENTS

| | | |
|---|---|---|
| 8,112,160 B2 | 2/2012 | Foster |
| 2002/0183820 A1 | 12/2002 | Schell |
| 2003/0040787 A1 | 2/2003 | Flynn et al. |
| 2003/0144721 A1 | 7/2003 | Villaseca et al. |
| 2007/0179582 A1 | 8/2007 | Marshall et al. |
| 2007/0299493 A1 | 12/2007 | Osypka |
| 2010/0100145 A1* | 4/2010 | Min .................. 607/17 |
| 2010/0145405 A1 | 6/2010 | Min et al. |
| 2010/0256701 A1 | 10/2010 | Muller |
| 2011/0022111 A1 | 1/2011 | Min |
| 2011/0125240 A1 | 5/2011 | Zhao et al. |
| 2011/0301676 A1 | 12/2011 | Zhang et al. |

OTHER PUBLICATIONS

Written Opinion—Parent Case—Intern'l Application No. PCT/EP2011/058982.

* cited by examiner

METHOD AND SYSTEM FOR STIMULATING A HEART

FIELD OF THE INVENTION

The present invention relates generally to implantable medical devices and more particularly to systems and methods for stimulating a heart of a patient.

BACKGROUND OF THE INVENTION

Cardiac resynchronization therapy (CRT) has been proven to be a good method to help patients with congested heart failure and bundle branch block. The optimal ventricular stimulation delay (VV-delay) is often selected by use of echocardiography or invasive LV dP/dt (max) measurements.

When using echocardiography, lateral movements of the interventricular septum indicate a suboptimal VV-delay. When the biventricular stimulation is performed with an optimal VV-delay, the septal movements laterally are minimized. Thus, if the propagation times from the right and left ventricles to the AV node in the septum is different, this can be compensated by a programmed VV-delay that ensures simultaneous arrival of the action potential to the septum.

Measuring left ventricular pressure gradient is an invasive procedure that only can be performed at a clinic. When septal movements are minimized the LV contractions are the most efficient which gives the highest dP/dt(max).

Neither echocardiography nor invasive pressure measurements can be performed outside clinic, which makes it difficult to continuously optimize the VV-delay in patients treated with cardiac resynchronization therapy (CRT).

The optimal VV-delay used for CRT will be changing over time due to remodelling and disease progression. Continuous optimization would therefore improve the cardiac function in long term and speed up the reverse remodelling process after start of therapy. The response to CRT would also be beneficial as the optimal setting always would be programmed in the device.

Thus, efforts have been made within the art to provide solutions for out-of-clinic methods and systems for continuous optimization of VV-delay and/or atrio-ventricular pacing delays (e.g. AV-delay or PV-delay).

St. Jude Medical's QuickOpt™ Timing Cycle Optimization is an algorithm that provides IEGM (Intracardiac Electrogram) based AV (Atrial-Ventricular) timing optimization in CRT and ICD (Implantable Cardioverter-Defibrillator) systems and VV (Ventricular-Ventricular) timing optimization in CRT devices in a simple and swift way. QuickOpt™ Timing Cycle Optimization is based on the hypothesis that the point of time for the closure of the Mitral valve can be estimated by measuring the interatrial conduction time (P-wave duration), that the onset of isovolumetric contraction can be measured using the peak of the R-wave and that interventricular conduction delays can be measured by evaluating simultaneous RV (Right Ventricular) and LV (Left Ventricular) IEGMs and measuring the time between the peaks of the R-waves. The goal is to characterize interatrial conduction patterns so that preload is maximized and ventricular pacing does not occur until after full closure of the mitral valve and to characterize intrinsic and paced interventricular conduction patterns so that pacing stimuli and the resultant LV and RV conduction (paced wave fronts) meet at the ventricular septum. Accordingly, QuickOpt™ Timing Cycle Optimization electrically characterizes the conduction properties of the heart to calculate optimal AV delay, PV delay (the time interval between a sensed atrial event and the ventricular impulse) and VV delay. QuickOpt™ Timing Cycle Optimization has been clinically proven to correlate with the more time-consuming echo-based methods and may be used for patients carrying CRT and dual-chamber devices at implant or follow up. QuickOpt™ Timing Cycle Optimization is an appealing optimization method since it does not require systematic measurements of a number of different AV and VV delays, which makes it very fast and simple. There are other IEGM based optimization methods among which QuickOpt™ Timing Cycle Optimization is one such method.

U.S. Pat. Appl. 2010/0145405 to Min et al., entitled "Systems and methods for controlling ventricular pacing in patients with long inter-atrial conduction delays", presents a solution using QuickOpt™. In particular, atrio-ventricular conduction delays are measured and used for determining the pacing regime.

In U.S. Pat. Appl. 2010/0256701 to Muller, entitled "Determining site-to-site pacing delay for multi-site anti-tachycardia pacing", a solution where interventricular delays are determined for use in anti-tachycardia pacing is disclosed. A left to right directional conduction time is determined, for example, an LV lateral wall to RV apex time, by delivering energy to a LV lateral wall site, by sensing the delivered energy at a RV apex site and by measuring the elapsed time. The RV apex to LV lateral wall time is thereafter determined. A pacing regime is determined based on an offset between these two time intervals.

In U.S. Pat. Appl. 2011/0022111 to Min, entitled "Systems and methods for optimizing ventricular pacing delays during atrial fibrillation", methods and devices for optimizing interventricular (VV) pacing delays during AF (Atrial Fibrillation) are disclosed. A test to detect an intrinsic interventricular conduction delay for determining an optimal VV delay is performed. The test is initiated upon detection of AF based on high atrial rate. More specifically, separate RV pace and LV pace tests are performed to determine interventricular delays for left and right side (i.e. left to right conduction delay and vice versa). A RV test can be performed by first detecting RR intervals between RV QRS complexes on the RV channel. Then, RV pacing intervals are set to a period shorter than the detected RR intervals (e.g. 95% to 98% of the detected RR interval) to secure that the resulting LV QRS will arise via interventricular conduction and not via AV conduction from the atria. Right to left conduction delay is determined based on time delays between sequences of RV pacing pulses and respective detected resulting LV QRS's. For example, an average right to left conduction delay can be determined by averaging a set of such time delays. A similar procedure is performed to determine the corresponding time delay from left to right.

However, there is still a need within the art of improved systems and methods for continuous and automatic optimization of VV-delays of an implanted cardiac stimulator such as a pacemaker.

SUMMARY OF THE INVENTION

An object of the present invention is to provide a system, and a method for further improvements in optimization of VV delays for use in, for example, CRT.

This and other objects of the present invention are achieved by means of an implantable medical device and a method having the features defined in the independent claims. Embodiments of the invention are characterized by the dependent claims.

According to an aspect of the present invention there is provided a method for determining cardiac pacing therapy using an implantable cardiac stimulation device. The method comprises activating a first ventricle by delivering stimulation to at least one stimulation site, estimating a point of time for arrival at the AV node for at least one depolarization wave resulting from the stimulation in the first ventricle and computing a first activation time interval substantially corresponding to the time interval required for at least one depolarization wave to travel from the stimulation site in the first ventricle to the AV node using the estimated point of time for arrival of the depolarization wave and a point of time for delivery of stimulation. Thereafter, the other ventricle is stimulated by delivering stimulation to at least one stimulation site. A point of time for arrival at the AV node for at least one depolarization wave resulting from the stimulation in the other ventricle is then estimated and a second activation time interval substantially corresponding to the time required for at least one depolarization wave to travel from the stimulation site in the other ventricle to the AV node using the estimated arrival of the depolarization wave and the point of time for delivery of stimulation is computed. Based on these activation time intervals and a difference between the intervals, a pacing therapy can be determined, wherein the first ventricle is paced prior to activation of the other ventricle if the activation time difference indicates that the first activation time interval is longer than the second activation time interval and the other ventricle is paced prior to activation of the first ventricle if the activation time difference indicates that the second activation time interval is longer than the first activation time interval.

According to another aspect of the present invention there is provided a system for determining cardiac pacing therapy of a patient in which an implantable cardiac stimulation device is implanted. The system comprises a pacing module configured to provide pacing signals for delivery to the patient via medical leads including electrodes connectable to the pacing module, wherein at least one electrode is positioned in each ventricle for activating respective ventricle by delivering stimulation to at least one stimulation site. Furthermore, an estimating module is configured to estimate a point of time for arrival at the AV node for at least one depolarization wave resulting from a stimulation in a ventricle and an activation time interval computing module is configured to compute activation time intervals substantially corresponding to the time interval required for at least one depolarization wave to travel from the stimulation site in a ventricle to the AV node using the estimated arrival of the depolarization wave and a point of time for delivery of stimulation. The system further includes a ventricular pacing controlling module configured to determine a pacing therapy based on an activation time difference between the a first and second activation time interval, wherein the first activation time interval corresponds to the time required for at least one depolarization wave to travel from the stimulation site in a first ventricle to the AV node and the second activation time interval corresponds to the time required for at least one depolarization wave to travel from the stimulation site in the other ventricle to the AV node, the pacing therapy comprising pacing the first ventricle prior to activation of the other ventricle if the activation time difference indicates that the first activation time interval is longer than the second activation time interval and pacing the other ventricle prior to activation of the first ventricle if the activation time difference indicates that the second activation time interval is longer than the first activation time interval.

Thus, the present invention is based on the insight that the AV node can be used as a substitute for septum with regard arrival of depolarization waves. In certain prior art optimization methods, such as QuickOpt™ optimization of VV-delay is based on the hypothesis that septum should be reached at the same time when stimulating both right ventricle and left ventricle. However, the inventors have found that an alternative and accurate method of optimizing VV-delays can instead be based on that the AV node should be reached at the same time when stimulating both right ventricle and left ventricle. Since the AV node is not directly observable, the arrival to the AV node of a depolarization wave arising from stimulation in left or right ventricle has to be estimated. To this end, according to embodiments of the present invention, this estimation can be based on detecting depolarization waves using at least one electrode positioned in close vicinity to HIS bundle, in close vicinity to the orifice of the coronary sinus, or in right or left atrium. In the embodiments of the present invention using at least one electrode positioned in close vicinity to the orifice of the coronary sinus, or in right or left atrium, retrograde conduction through the AV-node is observed. The conduction time in atrium is the same irrespective whether the depolarization wave originates in left or right ventricle, which is utilized in the present invention in the comparison between depolarization waves. That is, a difference between a depolarization wave originating in the left ventricle detected close to orifice of Coronary Sinus or in left or right atrium and a depolarization wave originating in the right ventricle detected close to orifice of Coronary Sinus or in left or right atrium is the result of differences in conduction time in the respective ventricle. Hence, the respective times are compared and the propagation time spent in septum and atrium should be the same in both cases and a remaining difference is therefore due to different propagation times in the ventricles. If it takes longer for a LV stimulation to reach the AV node (i.e. for depolarization wave resulting from a stimulation in LV), LV should be stimulated first and the right ventricle should be stimulated with a time difference equal to the aforementioned time difference.

However, in case of atrial fibrillation, the retrograde conduction cannot be observed as an atrial signal. Instead, the parts of ventricular septum being in close vicinity to HIS bundle and the AV node can be surveyed. This may be accomplished, for example, by an electrode screwed into the valve plane at close vicinity to HIS bundle and the AV node. Thereby, electrical activity in high septum can be detected. This is beneficial in case of permanent or temporary atrial fibrillation. After a stimulation pulse delivered in left of right ventricle, a depolarization wave is spread across the myocardium and eventually reaches HIS bundle and the AV node. The respective time from stimulation in left and right ventricle to detection of the resulting depolarization wave by an electrode positioned in close vicinity to HIS bundle and AV node is measured and registered. The respective times are compared and the propagation time spent in septum should be the same in both cases and a remaining difference is therefore due to different propagation times in the ventricles. If it takes longer for a LV stimulation to reach the AV node (i.e. for depolarization wave resulting from a stimulation in LV), LV should be stimulated first and the right ventricle should be stimulated with a time difference equal to the aforementioned time difference.

In the embodiments based on retrograde conduction, it is necessary to identify a time window when the AV node is capable of retrograde conduction. Retrograde P-waves are, for example, frequently seen after a PVC (Premature Ventricular Contraction). After an atrial contraction, the stimulation device waits for an anterograde ventricular depolarization. After short period of time, a stimulation pulse is delivered in RV or LV. A depolarization wave is spread across the myocardium and eventually reaches the AV node. If properly timed, this will result in a retrograde conduction through the AV node and a propagated atrial wave. After some time, this retrograde P-wave will be detected by an atrial electrode. The time from RV or LV to RA/LA is measured and registered. This process is repeated but the stimulation is delivered in the other ventricle. The new V-to-A time is registered and compared with the former one. The propagation time spent in the atrium is equal in both cases, so the remaining difference is due to different propagation times in the ventricles. If it takes longer for a LV stimulation to reach the AV node (i.e. for depolarization wave resulting from a stimulation in LV), LV should be stimulated first and the right ventricle should be stimulated with a time difference equal to the aforementioned time difference.

When optimizing based on V-to-A times, it is essential that the P-wave detected as retrograde is not a sinus node released P-wave. In order to prevent this from occurring, the sinus rhythm (i.e. the P-P interval) is detected a short period before the conduction time measurements for comparison analysis. Furthermore, it is also advantageous if the rhythm is stable and low, preferably at rest.

According to a preferred embodiment of the present invention, the optimization of VV-delays is performed based on retrograde conduction time differences. The sinus rhythm is monitored to identify a stable rhythm and the P-P interval is registered. The ventricles are stimulated with an interval shorter than the previously registered P-P interval and the stimulation is continued until stable retrograde P-waves are achieved. This is detected by observing the time from V-spike to P-wave. Retrograde P-waves are present when the time from V-spike to detected P-wave is constant. Thereafter, the right and left ventricle are stimulated one at a time using the same interval. Thereby, two retrograde P-waves have been generated, one originating from the right ventricle and one from the left ventricle. The retrograde P-waves are detected and the time intervals between the respective stimulation and respective detection of the subsequent P-wave. A new VV-delay can thereafter be calculated based on the difference between the time intervals.

According to embodiments of the present invention, depolarization waves are detected using at least one electrode positioned in a region in close vicinity to HIS bundle and the valve plane defined by an imaginary approximate half circle below the valve plane having a radius of about 10 mm, the half circle starting at the valve plane on right ventricle side, crossing septum below the valve plane, reaching the valve plane on left ventricle side and ending at the starting point on the right ventricle side. The point in time for detection of the at least one depolarization wave is estimated as the point of time for arrival at the AV node. The region may also be defined as a region within a distance of 0-20 mm from HIS bundle and below the valve plane.

According to embodiments of the present invention, an electrode can be positioned close to HIS bundle using a procedure as follows: (i) detecting HIS potential at an electrode positions close to the valve plane and septum; (ii) determining an approximate location of HIS bundle to correspond to the position of the electrode detecting HIS potential; and (iii) positioning at least one electrode within a region defined by imaginary approximate half circle-like line below the valve plane having a distance to the approximate location of HIS bundle of about 10 mm or at distance of 0-20 mm from HIS bundle and below the valve plane.

According to embodiments of the present invention, the depolarization waves are detected using an electrode positioned in the orifice of coronary sinus or within a distance of about 20 mm from the orifice of coronary sinus and in coronary sinus and the point in time for detection of the at least one depolarization wave is estimated as the point of time for arrival at the AV node. To verify this estimation, retrograde depolarization waves can be detected using the electrode positioned in the orifice of coronary sinus or within a distance of about 20 mm from the orifice of coronary sinus and in coronary sinus. The point in time for detection of the at least one retrograde depolarization wave is estimated as the point of time for arrival at the AV node and the activation time interval difference between the first and second activation time intervals for the depolarization waves resulting from a stimulation in the first and other ventricle, respectively, is compared with an activation time interval difference between the first and second activation time intervals for the retrograde depolarization waves corresponding to the same stimulation in the first and other ventricle. If the activation time intervals differences are substantially equal, determining that the activation time interval difference between the first and second activation time intervals for the depolarization waves was correctly determined.

According to embodiments of the present invention, retrograde depolarization waves resulting from the stimulation in the first or other ventricle can be detected using an electrode positioned in right or left atrium. The point in time for detection of the at least one depolarization wave can be estimated as the point of time for arrival at the AV node.

According to embodiments of the present invention, a subsequent depolarization event due to retrograde conduction is distinguished from a sinus node induced depolarization by: (i) detecting a P-wave interval of the sinus rhythm during a period prior to a determination of first and second activation time intervals; and (ii) delivering the stimulation to the ventricles using a shorter interval than an P-wave interval of the detected sinus rhythm.

According to embodiments of the present invention, the optimization using retrograde conduction further comprises: (i) delivering pacing pulses to left and right ventricle; (ii) monitoring atrial events following the delivered ventricle pacing pulses in left and/or right atrium using at least one electrode positioned in left and/or right atrium; and (iii) determining a respective activation time between a delivered ventricular pacing pulse in left and right ventricle and a subsequent atrial event, wherein a session for determining a pacing therapy is initiated if the activation time between a delivered ventricular pacing pulse and a subsequent atrial event is found to be stable during a predetermined period of time.

Further objects and advantages of the present invention will be discussed below by means of exemplifying embodiments.

These and other features, aspects and advantages of the invention will be more fully understood when considered with respect to the following detailed description, appended claims and accompanying drawings.

BRIEF DESCRIPTION OF THE DRAWINGS

Exemplifying embodiments of the invention are illustrated by way of example and not by way of limitation in the figures of the accompanying drawings in which like references indicate similar elements. It should be noted that references to "an" or "one" embodiment in this discussion are not necessarily to the same embodiment, and such references mean at least one.

DESCRIPTION OF EXEMPLIFYING EMBODIMENTS

The following is a description of exemplifying embodiments in accordance with the present invention. This description is not to be taken in limiting sense, but is made merely for the purposes of describing the general principles of the invention. It is to be understood that other embodiments may be utilized and structural and logical changes may be made without departing from the scope of the present invention.

According to the present invention, the VV-delay optimization is preferably performed, generally described, by using a right ventricular tip electrode (or a right ventricular ring electrode) and the left ventricular tip electrode (or a left ventricular ring electrode) for delivering stimulation pulses and by using an electrode placed in close vicinity to HIS bundle, in close vicinity to the orifice of the Coronary Sinus or in left or right atrium for detecting the resulting depolarization wave as will be described below with reference to FIG. 1-4.

Figure 1:
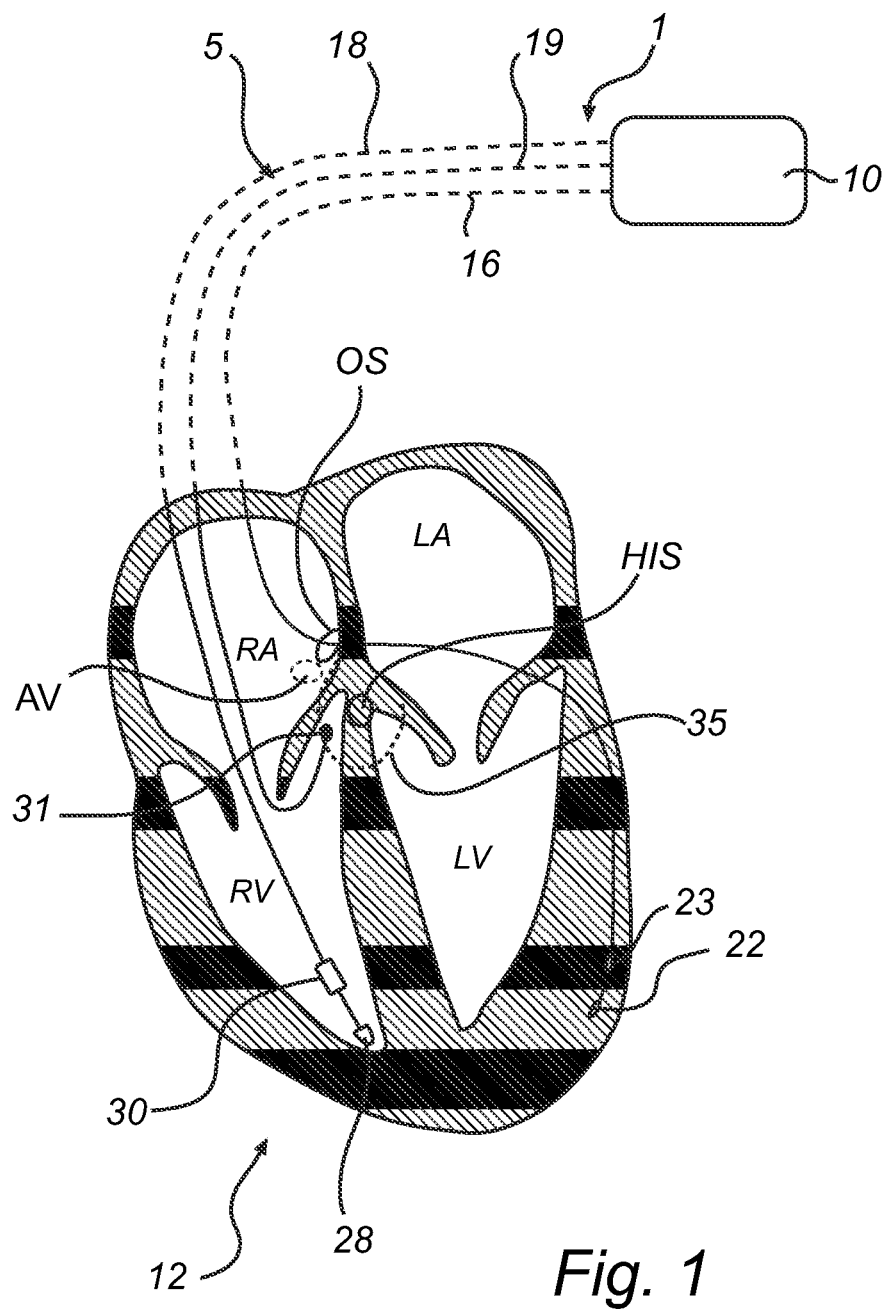
FIG. 1 is a simplified and schematic diagram of one embodiment of a system configuration according to the present invention including an implantable stimulation device in electrical communication with several leads implanted in a patient's heart for detecting cardiac activity and for delivering multi-chamber stimulation. The illustrated embodiment includes an electrode placed in close vicinity to HIS bundle.
Figure 2:
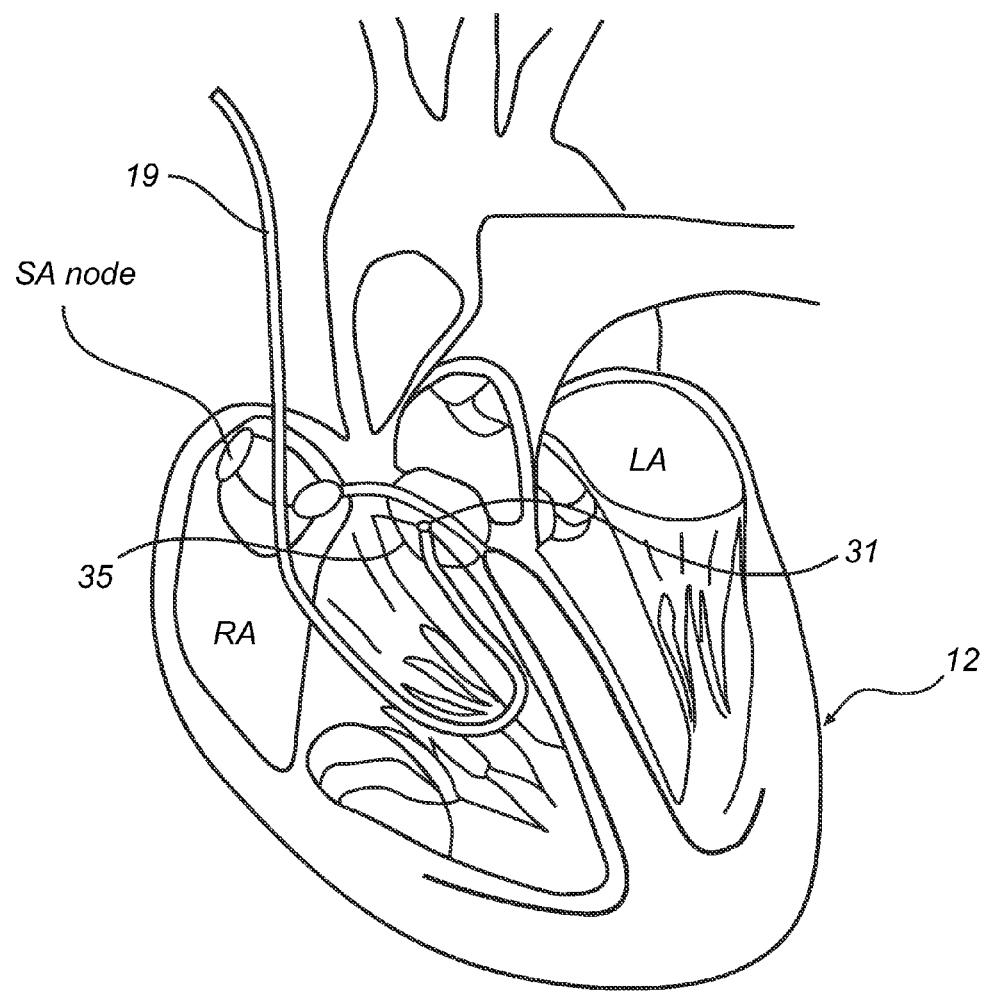
FIG. 2 shows another view of the placement of an electrode in close vicinity to HIS bundle.

Referring first to FIGS. 1 and 2, one embodiment of the present invention relating to a system including an implantable cardiac stimulator connectable to one or more medical leads will be discussed.

The implantable cardiac stimulator 10 of the system 1 is in electrical communication with a patient's heart 12 by way of leads 5, in this embodiment by way of three leads 16, 18 and 19 suitable for detecting cardiac activity and delivering multichamber stimulation therapy.

To sense left atrial and ventricular cardiac signals and to provide left chamber pacing therapy the stimulator is coupled to a coronary sinus lead 16 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible via the coronary sinus.

The lead 16 is designed to receive ventricular cardiac signals and to deliver left ventricular pacing therapy using a left ventricular tip electrode 22. However, the lead 16 may also include further ventricular electrodes, such as a left ventricular ring electrode 23 and may also deliver left atrial pacing therapy using, for example, a left atrial ring electrode 24.

The cardiac stimulator 10 is also in electrical communication with the heart 12 by way of an implantable right ventricular lead 18 having, in this embodiment, a right ventricular tip electrode 28 and/or a right ventricular ring electrode 30. Typically, the right ventricular lead 18 is transvenously inserted into the heart 12 to place the right ventricular tip electrode 28 in the right ventricular apex. The right ventricular lead 18 is capable of sensing or receiving cardiac signals, and delivering stimulation in the form of pacing therapy.

In this embodiment, a second implantable right ventricular lead 19 connected to the cardiac stimulator 10 is in electrical communication with the heart 12. The second right ventricle lead 19 includes a second right ventricular tip electrode 31 positioned in a region in close proximity to HIS bundle, the valve plane and ventricular septum. HIS bundle is schematically indicated by HIS and the orifice of Coronary Sinus is indicated by OS.

Preferably, the second right ventricular tip electrode 31 is positioned at an approximate distance from a centre of HIS bundle of 0-20 mm. This may also be defined as a region in close vicinity to HIS bundle and the valve plane defined by, for example, half circle line below the valve plane having a radial distance to HIS bundle of about 20 mm. In FIG. 1, this region is schematically indicated by the dashed line 35.

In FIG. 2, the placement of the electrode 31 is shown in another view. Note that in FIG. 2, for clarifying purposes, only the lead 19 including the electrode 31 is shown.

A VV-delay optimization can be performed using this embodiment of the system according to the present invention by delivering stimulation in the left and right ventricle via the electrodes 22 and 28, respectively, and estimating the respective time interval from the stimulations to detection of a resulting depolarization wave arriving at the AV node (schematically indicated by AV). In the embodiment shown in FIG. 1, the arrival of the resulting depolarization wave at the AV node, AV, is estimated by detecting the arrival of the resulting depolarization wave at the electrode 31 positioned in close vicinity to HIS bundle. This will be described in more detail below with reference to FIG. 6.

Figure 3:
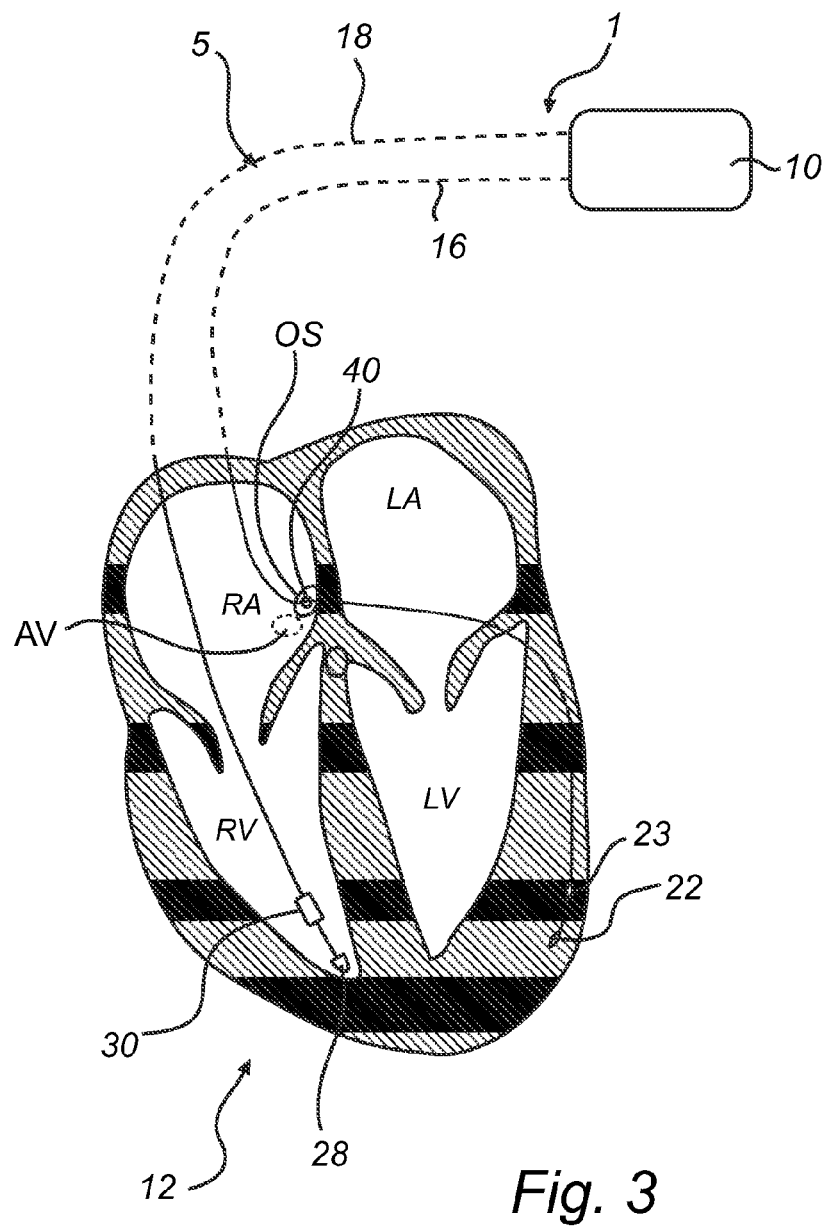
FIG. 3 is a simplified and schematic diagram of another embodiment of a system configuration according to the present invention including an implantable stimulation device in electrical communication with several leads implanted in a patient's heart for detecting cardiac activity and for delivering multi-chamber stimulation. The illustrated embodiment includes an electrode placed in close vicinity to the orifice of Coronary Sinus.

With reference now to FIG. 3, another embodiment of the present invention relating to a system including an implantable cardiac stimulator connectable to one or more medical leads will be discussed.

The implantable cardiac stimulator 10 of the system 1 is in electrical communication with a patient's heart 12 by way of leads 5, in this embodiment by way of two leads 16 and 18 suitable for detecting cardiac activity and delivering multi-chamber stimulation therapy.

To sense left atrial and ventricular cardiac signals and to provide left chamber pacing therapy the stimulator is coupled to a coronary sinus lead 16 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible via the coronary sinus.

The lead 16 is designed to receive ventricular cardiac signals and to deliver left ventricular pacing therapy using a left ventricular tip electrode 22. However, the lead 16 may also include further ventricular electrodes, such as a left ventricular ring electrode 23 and may also deliver left atrial pacing therapy using, for example, a left atrial ring electrode 24.

Furthermore, the lead 16 comprises an electrode 40 (e.g. a ring electrode) positioned in the orifice of Coronary Sinus, OS, or in close vicinity to the orifice in Coronary Sinus in Coronary Sinus, preferably within 20 mm from the orifice in Coronary Sinus.

The cardiac stimulator 10 is also in electrical communication with the heart 12 by way of an implantable right ventricular lead 18 having, in this embodiment, a right ventricular tip electrode 28 and/or a right ventricular ring electrode 30. Typically, the right ventricular lead 18 is transvenously inserted into the heart 12 to place the right ventricular tip electrode 28 in the right ventricular apex. The right ventricular lead 18 is capable of sensing or receiving cardiac signals, and delivering stimulation in the form of pacing therapy.

A VV-delay optimization can be performed using this embodiment of the system according to the present invention by delivering stimulation in the left and right ventricle via the electrodes 22 and 28, respectively, and estimating the respective time interval from the stimulations to detection of a resulting depolarization wave arriving at the AV node, AV. In the embodiment shown in FIG. 3, the arrival of a resulting depolarization wave at the AV node, AV, is estimated by detecting the arrival of the resulting depolarization wave at the electrode 40 positioned in the orifice of coronary sinus, OS, or within a distance of about 20 mm from the orifice of coronary sinus in the Coronary Sinus. To verify this estimation, retrograde depolarization waves can also be detected using the electrode positioned in the orifice of coronary sinus or within a distance of about 20 mm from the orifice of coronary sinus and in coronary sinus. The point in time for detection of the at least one retrograde depolarization wave is estimated as the point of time for arrival at the AV node and the activation time interval difference between the first and second activation time intervals for the depolarization waves resulting from a stimulation in the first and other ventricle, respectively, is compared with an activation time interval difference between the first and second activation time intervals for the retrograde depolarization waves corresponding to the same stimulation in the first and other ventricle. If the activation time intervals differences are substantially equal, determining that the activation time interval difference between the first and second activation time intervals for the depolarization waves was correctly determined.

Figure 4:
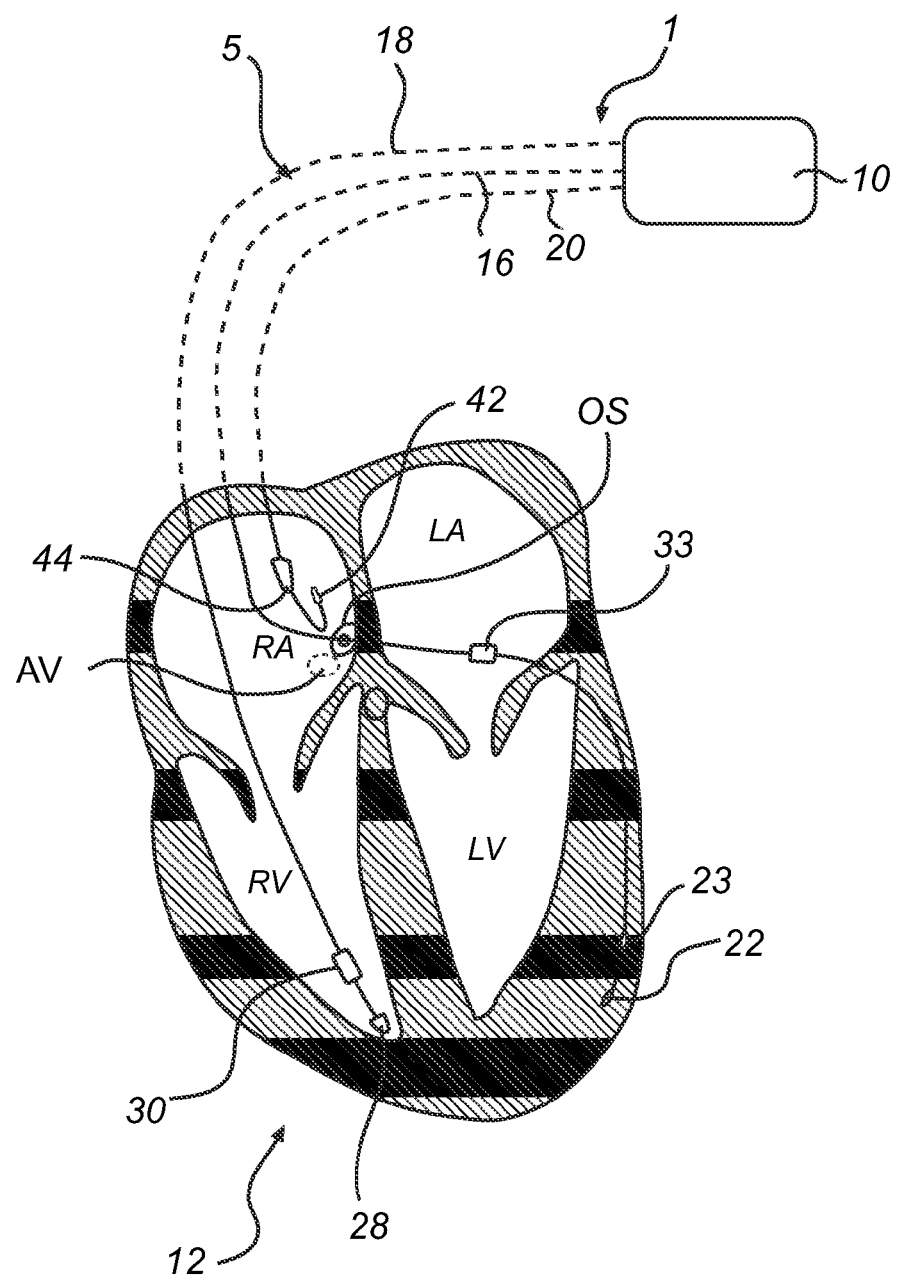
FIG. 4 is a simplified and schematic diagram of yet another embodiment of a system configuration according to the present invention including an implantable stimulation device in electrical communication with several leads implanted in a patient's heart for detecting cardiac activity and for delivering multi-chamber stimulation. The illustrated embodiment includes an electrode placed in left of right atrium.

With reference to FIG. 4, a further embodiment of the present invention relating to a system including an implantable cardiac stimulator connectable to one or more medical leads will be discussed.

The implantable cardiac stimulator 10 of the system 1 is in electrical communication with a patient's heart 12 by way of leads 5, in this embodiment by way of three leads 16, 18 and 20 suitable for detecting cardiac activity and delivering multichamber stimulation therapy.

To sense left atrial and ventricular cardiac signals and to provide left chamber pacing therapy the stimulator is coupled to a coronary sinus lead 16 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible via the coronary sinus.

The lead 16 is designed to receive ventricular cardiac signals and to deliver left ventricular pacing therapy using a left ventricular tip electrode 22. However, the lead 16 may also include further ventricular electrodes, such as a left ventricular ring electrode 23 and may also deliver left atrial pacing therapy using, for example, a left atrial ring electrode 33.

The cardiac stimulator 10 is also in electrical communication with the heart 12 by way of an implantable right ventricular lead 18 having, in this embodiment, a right ventricular tip electrode 28 and/or a right ventricular ring electrode 30. Typically, the right ventricular lead 18 is transvenously inserted into the heart 12 to place the right ventricular tip electrode 28 in the right ventricular apex. The right ventricular lead 18 is capable of sensing or receiving cardiac signals, and delivering stimulation in the form of pacing therapy.

A right atrial lead 20 is positioned in and/or passes through the right atrium. The stimulation device 10 is coupled to the right atrial lead 20 including a right atrial tip electrode 42, which is typically implanted in the patient's right atrial appendage. The right atrial lead may also include an atrial ring electrode 44. According to the present invention, the right atrial electrode 42 and/or 44 is/are used inter alia to detect retrograde depolarization waves resulting from delivered stimulation in the ventricles. In an alternative embodiment of the present invention, a right atrial ring electrode may be arranged on the lead 16 passing through the right atrium to provide the possibility to detect retrograde conduction.

A VV-delay optimization can be performed using this embodiment of the system according to the present invention by delivering stimulation in the left and right ventricle via the electrodes 22 and 28, respectively, and estimating the respective time interval from the stimulations to detection of a resulting depolarization wave arriving at the AV node, AV. In the embodiment shown in FIG. 3, the arrival of the resulting retrograde depolarization wave at the AV node, AV, is estimated by detecting the arrival of the resulting depolarization wave at the right atrium electrode 42 (or the electrode 44).

In an alternative embodiment, it may be possible to use the left atrium electrode 24 to detect the retrograde depolarization waves resulting from the stimulation in the right and left ventricles.

Figure 5:
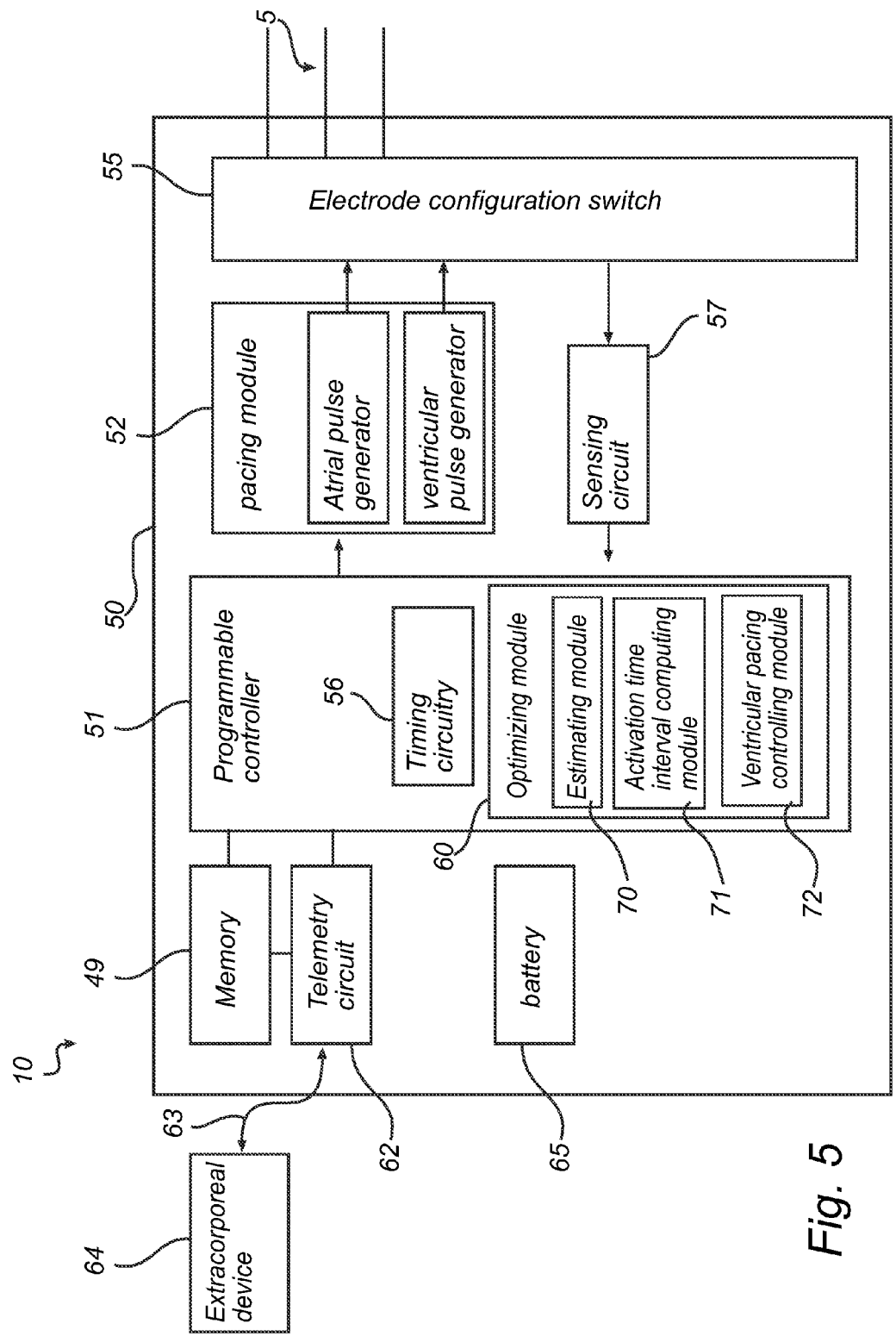
FIG. 5 is a simplified functional block diagram of one embodiment of a system in accordance with the present invention, illustrating basic elements of the system.

Turning now to FIG. 5, a cardiac stimulator for use in the system according to the present invention will be discussed. FIG. 5 discloses an exemplary, simplified block diagram depicting various components of the cardiac stimulator according to embodiments of the present invention is shown.

The cardiac stimulator 10 is capable of delivering cardiac resynchronization therapy (CRT) and is configured to integrate both monitoring and therapy features, as will be described below. The cardiac stimulator 10 may collect and process data about the heart 12 from one or more sensors (not shown). Further, the cardiac stimulator 10 collects and processes data about the heart 12 from electrodes (see FIG. 1-4) for sensing cardiac electrogram (EGM) signals using, for example, any one of the electrode configurations shown in FIG. 1-4. While a particular multi-chamber device is shown, it is to be appreciated and understood that this is done for illustration purposes only. Thus, the techniques and methods described below can be implemented in connection with any suitable configured or configurable stimulation device. Accordingly, one of skill in the art could readily duplicate, eliminate, or disable the appropriate circuitry in any desired combination to provide a device capable of treating the appropriate chamber with pacing stimulation including cardiac resynchronisation therapy.

The cardiac stimulator 10 has a housing 50, often referred to as the "can" or "case electrode". The housing 50 may function as a return electrode in "unipolar" modes. Further, the housing 50 includes connector (not shown) having a plurality of terminals (not shown) for connection with electrodes and/or sensors.

The cardiac stimulator 10 includes a programmable microcontroller or control module 51 that inter alia controls the various modes of stimulation therapy. As well known within the art, the microcontroller 51 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 51 includes the ability to process or monitor input signals (data or information) as controlled by a program stored in a designated block of memory. The type of microcontroller is not critical to the described implementations. Rather, any suitable microcontroller 51 may be used that carries out the functions described herein. The use of micro-processor based control circuits for performing timing and data analysis are well known in the art.

Furthermore, the cardiac stimulator 10 includes pacing module 52 adapted to provide pacing signals for delivery to the patient. The pacing module 52 comprises an atrial pulse generator 53 and a ventricular pulse generator 54 that generate pacing stimulation pulses for delivery by leads 5, for example, by the coronary sinus lead 16, and/or the right ventricular lead 18 via an electrode configuration switch 55. It is understood that in order to provide stimulation therapy in each of the four chambers, the atrial and ventricular pulse generators 53 and 54, may include dedicated, independent pulse generators, multiplexed pulse generators, or shared pulse generators. The pulse generators 53 and 54 are controlled by the microcontroller 51 via appropriate control signals to trigger or inhibit stimulation pulses.

The microcontroller 51 further includes timing control circuitry 56 to control timing of the stimulation pulses (e.g. pacing rate, AV delay, VV delay, etc.) as well as to keep track of timing of refractory periods blanking intervals, etc. which is well known in the art. In addition, the microcontroller 51 may include components such as e.g. an arrhythmia detector (not shown) and/or a morphology detector (not shown).

Moreover, an optimization module 60 is configured to optimize VV delays. The optimization module 60 may be arranged in the microcontroller 51 or as a module coupled to the microcontroller 51. In embodiments of the present invention, the optimization module 60 comprises, as illustrated in FIG. 5, an estimating module 70 configured to estimate a point of time for arrival at the AV node for at least one depolarization wave resulting from a delivered stimulation pulse or set of pulses in a left or right ventricle. Further, the optimization module comprises an activation time interval computing module 71 configured to compute activation time intervals substantially corresponding to the time required for at least one depolarization wave to travel from a stimulation site in a left or right ventricle to the AV node using the estimated arrival of the depolarization wave and the point of time for delivery of stimulation and a ventricular pacing controlling module 72 configured to determine a pacing therapy based on an activation time difference between first and second activation time intervals. The first activation time interval corresponds to the time required for at least one depolarization wave to travel from a stimulation site in a first ventricle (e.g. the left ventricle) to the AV node and the second activation time interval corresponds to the time required for at least one depolarization wave to travel from a stimulation site in the other ventricle (e.g. the right ventricle) to the AV node. The ventricular pacing controlling module 72 is configured to determine a pacing therapy comprising pacing the first ventricle prior to activation of the other ventricle if the activation time difference indicates that the first activation time interval is longer than the second activation time interval and pacing the other ventricle prior to activation of the first ventricle if the activation time difference indicates that the second activation time interval is longer than the first activation time interval.

The aforementioned components may also be implemented as part of the microcontroller 51, or as software/firmware instructions programmed into the device and executed on the microcontroller 51 during certain modes of operation.

A sensing circuit 57 comprising atrial sensing circuits and ventricular sensing circuits may also be coupled to the leads 5, for example, the right atrial lead 20 or the coronary sinus lead 16 through the switch 55 for detecting the presence of cardiac activity in each of the four chambers of the heart. Accordingly, the atrial sensing circuits and ventricular sensing circuits 57 may include dedicated sense amplifiers, multiplexed amplifiers, or shared amplifiers.

The output from the atrial sensing circuits and ventricular sensing circuits 57 are connected to the microcontroller 41, which, in turn, is able to trigger or inhibit the atrial sensing circuits and ventricular sensing circuits 57 in a demand fashion in response to the absence or presence of cardiac activity in the appropriate chamber of the heart. In particular, output from the atrial sensing circuits and ventricular sensing circuits 57 is fed to the estimation module 70 for estimation of the arrival of depolarisation waves at the AV node, AV, for use in subsequent optimization of VV-delays.

Furthermore, the microcontroller 41 is coupled to a memory 49 by a suitable data/address bus (not shown), wherein the programmable operating parameters used by the microcontroller 41 are stored and modified, as required, in order to customize the operation of the cardiac stimulator to the needs of a particular patient. Such operating parameters define, for example, pacing pulse amplitude, pulse duration, etc. Advantageously, the operating parameters may be non-invasively programmed into the memory 49 through a communication module 62 including, for example, a telemetry circuit for telemetric communication via communication link 63 with an external device 64, such as a programmer or a diagnostic system analyzer. The telemetry circuit advantageously allows intra-cardiac electro-grams and status information relating to the operation of the device 10 to be sent to the external device 64 through an established communication link 63. Further, the communication module may alternatively or as a complement to the telemetry circuit include circuit for RF communication.

The cardiac stimulator 10 may further include a physiologic sensor (not shown), commonly referred to as a "rate-responsive" sensor because it is typically used to adjust pacing stimulation rate according to the exercise state of the patient. While shown as being included within the stimulator 10, it is to be understood that the physiologic sensor 56 also may be external to the stimulator, yet still be implanted within or carried by the patient. Examples of physiologic sensors include sensors that, for example, sense respiration rate, or activity variance.

Moreover, the cardiac stimulator 10 additionally includes a battery 65 that provides operating power to all of the circuits shown in FIG. 5. Preferably, the stimulator 10 employs lithium or similar battery technology.

Figure 6:
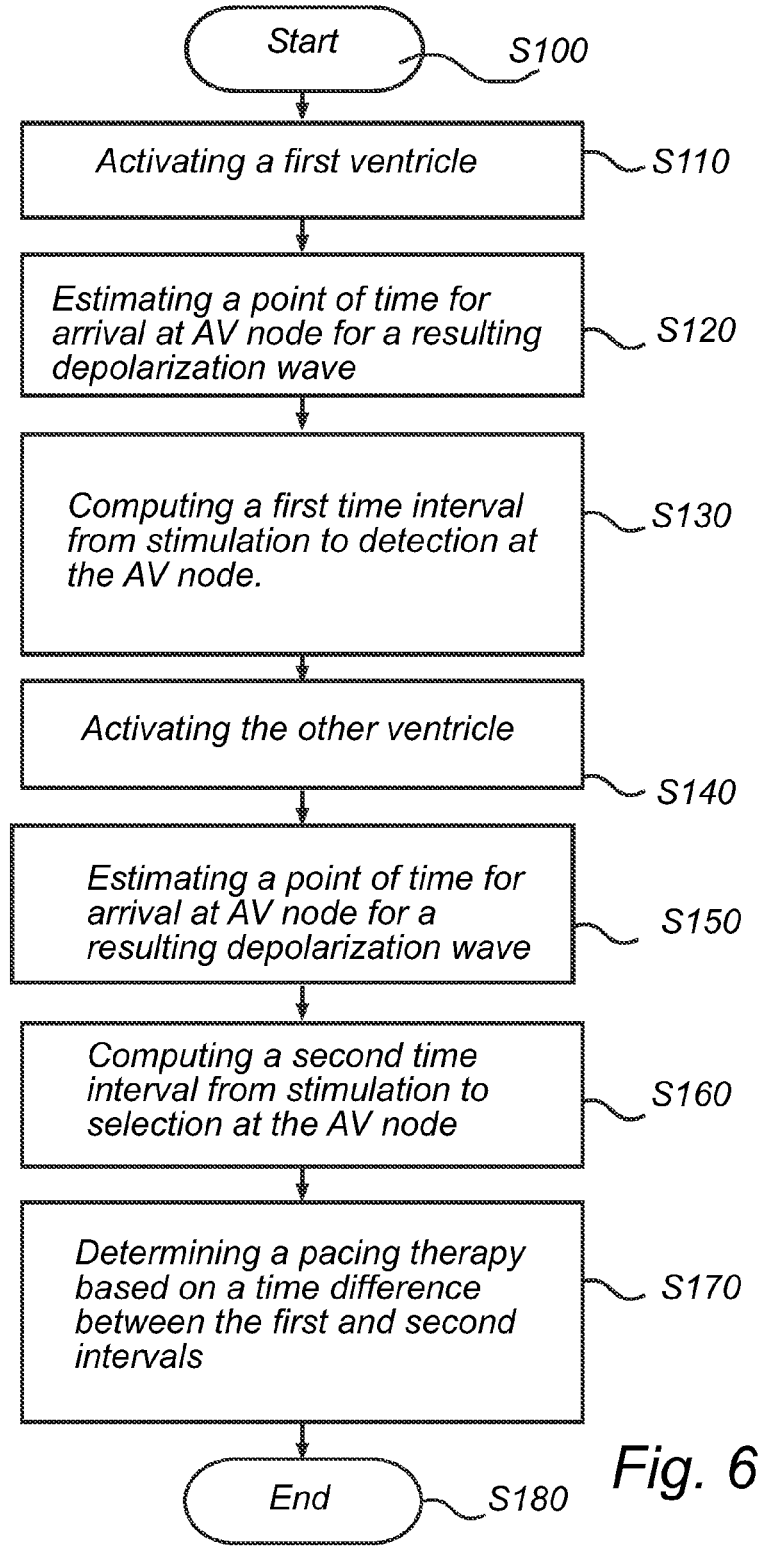
FIG. 6 is a flow chart illustrating the overall method for optimizing VV delays according to the present invention.

With reference now to FIG. 6, the general concept of the method for optimizing VV-delays according to the present invention will be discussed. FIG. 6 is a flow chart showing the general step of the method according to the present invention.

First, at step S100, an optimization procedure is started or initiated. The initiation of start of the procedure may, for example, be triggered at predetermined time intervals, at a predetermined cardiac event, or at receipt of an instruction, for example, from an external device 64. Furthermore, it is also preferred if a stable and low sinus rhythm is present when the optimization is performed, for example, when the patient is at rest.

Figure 10:
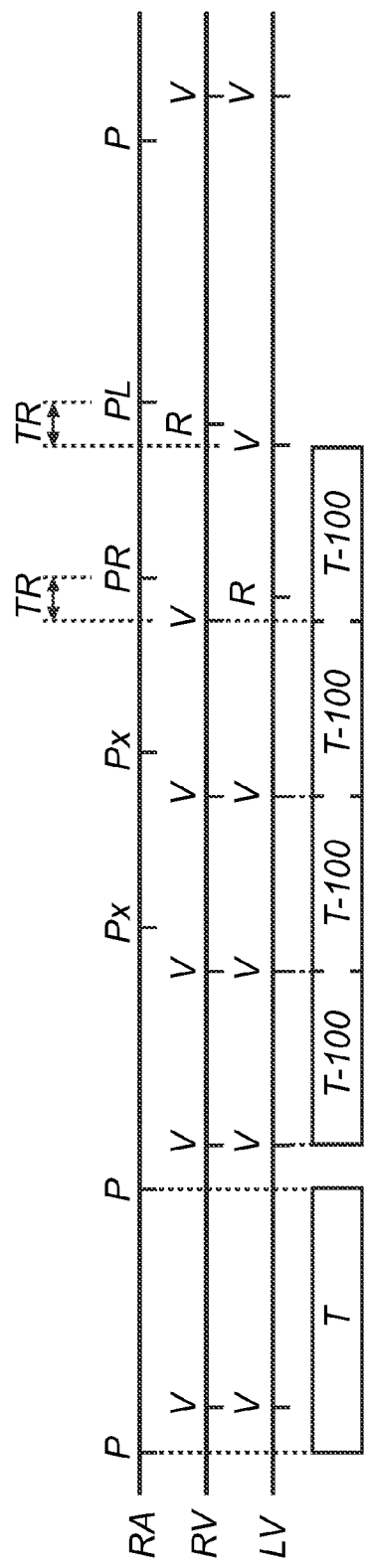
FIG. 10 is a diagram showing a stimulation interval being shorter than a measured P-P interval used for measurement of retrograde depolarization waves from RV and LV.

At step S110, a first ventricle is activated by delivering stimulation to at least one stimulation site, for example, the left ventricle by delivering stimulation via electrode 22. Preferably, the stimulation interval is shorter than a measured P-P interval at a stable and low rhythm, for example, about 100 ms shorter than the measured P-P interval. With reference to FIG. 10, it is shown how a stimulation interval T-100 is used. In FIG. 10, P indicates sinus P-wave, Px indicates unknown origin (sinus or retrograde), PR indicates retrograde P-wave from RV, PL indicates retrograde P-wave from LV. The time from stimulation in RV to PR is TR and the time from stimulation in LV to PL is TL.

Thereafter, at step S120, a point of time for arrival at the AV node for at least one depolarization wave resulting from the stimulation in the first ventricle is estimated. As has been described above, this can be achieved by detecting the depolarization wave by an electrode (e.g. electrode 31 in FIGS. 1 and 2) positioned in close vicinity to HIS bundle, HIS, or by detecting a retrograde conduction by an electrode positioned in close vicinity to the orifice of coronary sinus, OS, (e.g. electrode 40 in FIG. 3) or by an electrode in right or left atrium (e.g. electrode 42 in FIG. 4). If an electrode in the close vicinity to HIS bundle is used for the detection, the optimization can be performed for patients suffering from permanent or temporary AF.

At step S130, a first activation time interval is computed as substantially corresponding to the time required for at least one depolarization wave to travel from the stimulation site in the first ventricle to the AV node using the estimated arrival of the depolarization wave and the point of time for delivery of stimulation.

Subsequently, at step S140, the other ventricle is activated by delivering stimulation to at least one stimulation site. For example, the right ventricle can be activated by delivering stimulation via electrode 28. Preferably, the stimulation interval is shorter than a measured P-P interval at a stable and low rhythm, for example, about 100 ms shorter than the measured P-P interval. The interval in step S140 should be the same as the interval used in step S110.

At step S150, a point of time for arrival at the AV node for at least one depolarization wave resulting from the stimulation in the other ventricle is estimated using the same electrode as in step S120.

Thereafter, at step S160, the second activation time interval substantially corresponding to the time required for at least one depolarization wave to travel from the stimulation site in the other ventricle to the AV node can be computed by using the estimated arrival of the depolarization wave and the point of time for delivery of the stimulation.

At step S170, when the respective activation time intervals have been determined, a pacing therapy can be determined based on an activation time difference between the first and second activation time intervals. The pacing therapy comprises pacing the first ventricle prior to activation of the other ventricle if the activation time difference indicates that the first activation time interval is longer than the second activation time interval and pacing the other ventricle prior to activation of the first ventricle if the activation time difference indicates that the second activation time interval is longer than the first activation time interval. The optimization module 60 may instruct the pacing module 52 to implement the new VV-delay in its pacing regime.

When the pacing therapy has been determined, the optimization procedure is finalized at step S180 and the optimization module 60 is ready to execute a new optimization procedure so as to find a new and updated VV-delay.

Figure 7:
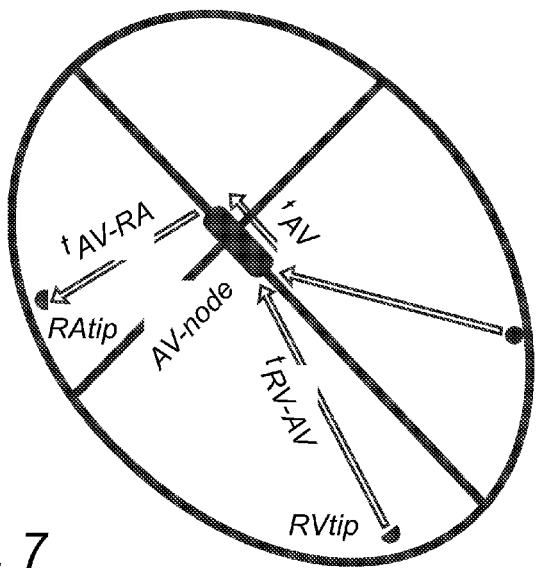
FIG. 7 schematically illustrates time propagation time intervals within a heart during retrograde conduction.
Figure 8:
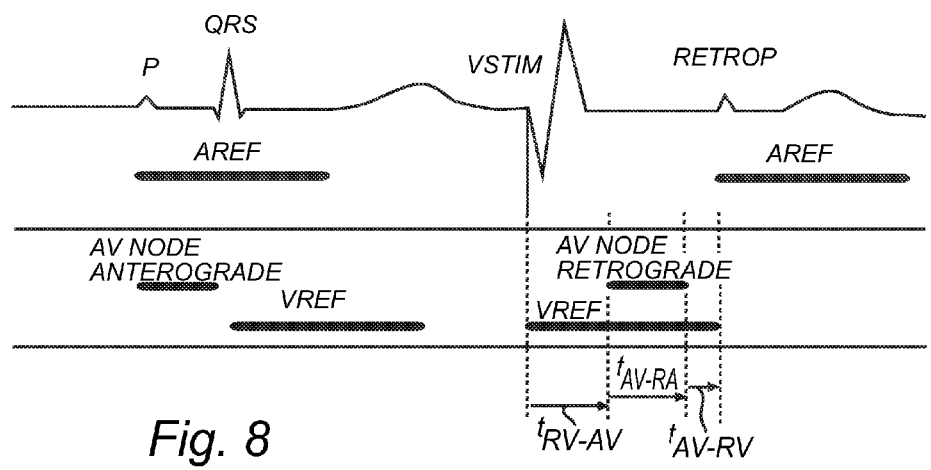
FIG. 8 schematically illustrates time intervals during retrograde conduction.

Turning now to FIGS. 7-10, optimization of VV-delays based on retrograde conduction time differences in accordance with an embodiment of the present invention will be discussed. Thus, the optimization is based on retrograde P-waves and times from RV or LV, respectively, to LA/RA is measured. This embodiment is based on that the propagation times spent in the atrium is equal in both cases which entails that the remaining difference is due to different propagation times in the ventricles. This is schematically illustrated in FIGS. 7 and 8.

Figure 9:
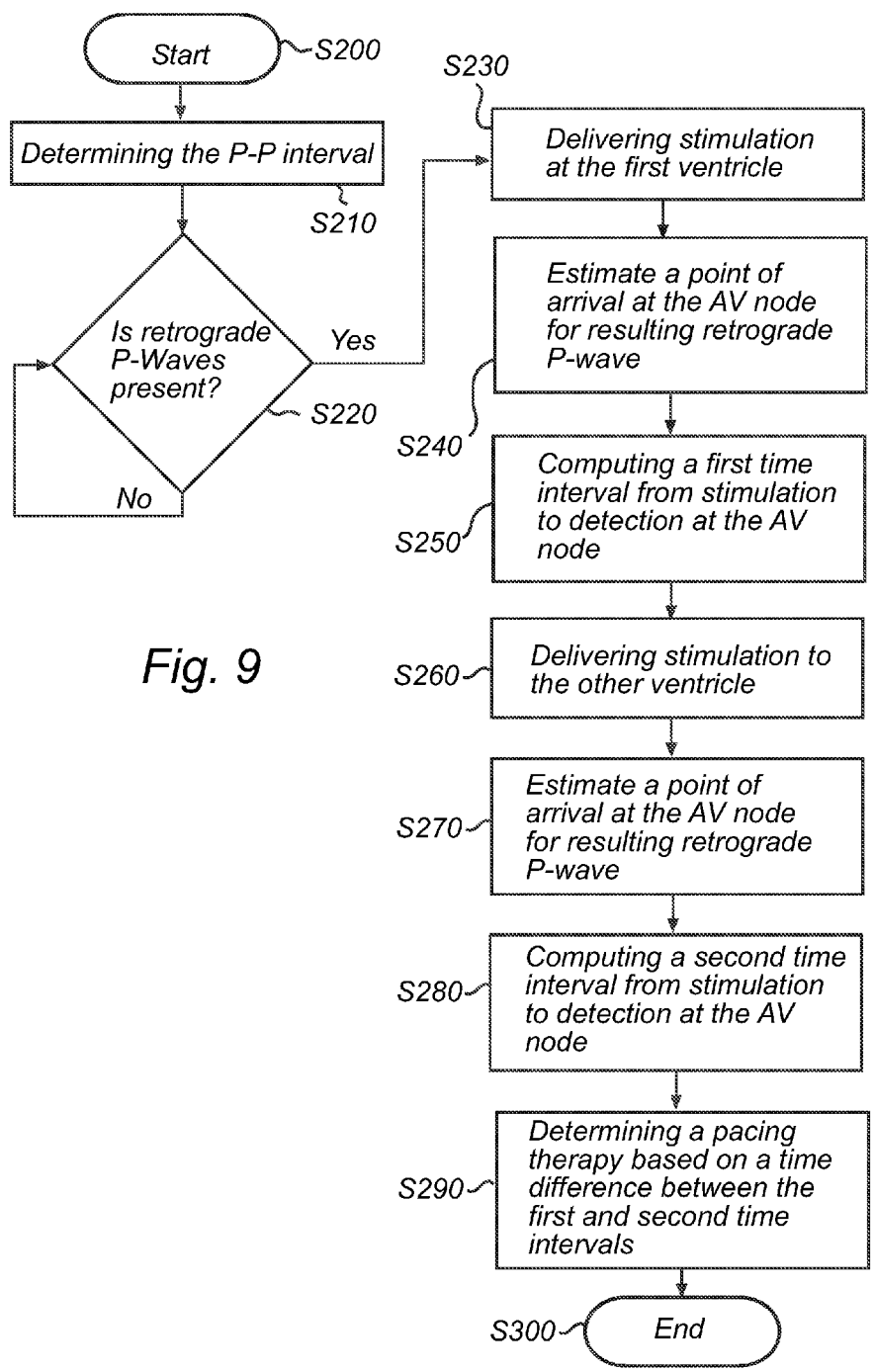
FIG. 9 is a flow chart illustrating an embodiment of the method for optimizing VV delays according to the present invention.

In FIG. 9, the steps of a method according to this embodiment are shown. First, at step S200, an optimization procedure is started or initiated. The initiation of start of the procedure may, for example, be triggered at predetermined time intervals, at a predetermined cardiac event, or at receipt of an instruction, for example, from an external device 64. Furthermore, it is also preferred if a stable and low sinus rhythm is present when the optimization is performed, for example, when the patient is at rest.

At step S210, the P-P interval is determined preferably at the stable sinus rhythm, which also may be performed before the optimization procedure is initiated.

Then, at step S220, the ventricles are stimulated with a shorter interval, T, than the previously measured P-P interval, see FIG. 10. The stimulation of the ventricles is continued until stable retrograde P-waves are achieved. This is detected by observing the time interval from the V-spike to detection of the P-wave using e.g. the electrode 42 positioned in right atrium. Retrograde P-waves are present when the time interval between the V-spike and the detected P-wave is constant. If retrograde P-wave not has been detected during a predetermined period of time, the procedure may be interrupted.

At step S230, stimulation is delivered at a first ventricle, e.g. the right ventricle via electrode 28, using the time interval T.

At step S240, the retrograde P-wave is detected using e.g. the electrode 42. That is, a point of time for arrival at the AV node for the depolarization wave resulting from the stimulation in the right ventricle is estimated.

At step S250, a first activation time interval substantially corresponding to the time interval required for the depolarization wave to travel from the stimulation site in the right ventricle to the AV node using the estimated point of time for arrival of the depolarization wave and a point of time for delivery of stimulation is computed.

In the next interval, at step S260, stimulation is delivered at the other ventricle, e.g. the left ventricle via electrode 22, using the time interval T.

At step S270, the retrograde P-wave is detected using e.g. the electrode 42. That is, a point of time for arrival at the AV node for the depolarization wave resulting from the stimulation in the right ventricle is estimated.

At step S280, a second activation time interval substantially corresponding to the time interval required for the depolarization wave to travel from the stimulation site in the ventricle to the AV node using the estimated point of time for arrival of the depolarization wave and a point of time for delivery of stimulation is computed.

Thereafter, a pacing therapy based on an activation time interval difference between the first and second activation time intervals is determined at step S290. The determined pacing therapy includes pacing the first ventricle prior to activation of the other ventricle if the activation time difference indicates that the first activation time interval is longer than the second activation time interval and the other ventricle is paced prior to activation of the first ventricle if the activation time difference indicates that the second activation time interval is longer than the first activation time interval.

Then, at step S300, the optimization procedure is finished. The optimization module 60 may instruct the pacing module 52 to implement the new VV-delay in its pacing regime. When the pacing therapy has been determined, the optimization procedure is thus finalized at step S300, and the optimization module 60 is ready to execute a new optimization procedure so as to find a new and updated VV-delay.

Hence, the sinus rhythm is monitored to identify a stable rhythm and the P-P interval is registered. The ventricles are stimulated with an interval shorter than the previously registered P-P interval and the stimulation is continued until stable retrograde P-waves are achieved. This is detected by observing the time from V-spike to P-wave. Retrograde P-waves are present when the time from V-spike to detected P-wave is constant. Thereafter, the right and left ventricle are stimulated one at a time using the same interval. Thereby, two retrograde P-waves have been generated, one originating from the right ventricle and one from the left ventricle. The retrograde P-waves are detected and the time intervals between the respective stimulation and respective detection of the subsequent P-wave. A new VV-delay can thereafter be calculated based on the difference between the time intervals Although certain embodiments and examples have been described herein, it will be understood by those skilled in the art that many aspects of the devices and methods shown and described in the present disclosure may be differently combined and/or modified to form still further embodiments. Alternative embodiments and/or uses of the devices and methods described above and obvious modifications and equivalents thereof are intended to be within the scope of the present disclosure. Thus, it is intended that the scope of the present invention should not be limited by the particular embodiments described above, but should be determined by a fair reading of the claims that follow.

The invention claimed is:

1. A method for determining cardiac pacing therapy using an implantable cardiac stimulation device, said method comprising:
   activating a first ventricle by delivering stimulation to at least one stimulation site;
   estimating a point of time for arrival at the AV node for at least one depolarization wave resulting from the stimulation of the first ventricle;
   computing a first activation time interval substantially corresponding to the time interval required for at least one depolarization wave to travel from the stimulation site of the first ventricle to the AV node using the estimated point of time for arrival of the depolarization wave and a point of time for delivery of stimulation;
   activating the other ventricle by delivering stimulation to at least one stimulation site;
   estimating a point of time for arrival at the AV node for at least one depolarization wave resulting from the stimulation of the other ventricle;
   computing a second activation time interval substantially corresponding to the time required for at least one depolarization wave to travel from the stimulation site in the other ventricle to the AV node using the estimated arrival of the depolarization wave and the point of time for delivery of stimulation; and
   determining a pacing therapy based on an activation time interval difference between the first and second activation time intervals, wherein the first ventricle is paced prior to activation of the other ventricle if the activation time difference indicates that the first activation time interval is longer than the second activation time interval and the other ventricle is paced prior to activation of the first ventricle if the activation time difference indicates that the second activation time interval is longer than the first activation time interval.

2. The method of claim 1, wherein estimating comprises:
   detecting at least one depolarization wave resulting from the stimulation of the first or other ventricle using at least one electrode positioned in a region in close vicinity to HIS bundle and the valve plane defined by an imaginary approximate half circle below the valve plane having a radius of about 10 mm, the half circle starting at the valve plane on right ventricle side, crossing septum below the valve plane, reaching the valve plane on left ventricle side and ending at the starting point on the right ventricle side; and
   estimating the point in time for detection of the at least one depolarization wave as the point of time for arrival at the AV node.

3. The method of claim 1, wherein estimating comprises:
   detecting at least one depolarization wave resulting from the stimulation of the first or other ventricle using at least one electrode positioned at distance of 0-20 mm from HIS bundle and below the valve plane; and
   estimating the point in time for detection of the at least one depolarization wave as the point of time for arrival at the AV node.

4. The method of claim 3, further comprising:
   detecting HIS potential at an electrode positioned close to the valve plane and septum;
   determining an approximate location of HIS bundle to correspond to the position of the electrode detecting HIS potential; and
   positioning at least one electrode within a region defined by imaginary approximate half circle-like line below the valve plane having a distance to the approximate location of HIS bundle of about 10 mm or at distance of 0-20 mm from HIS bundle and below the valve plane.

5. The method of claim 1, wherein estimating comprises:
   detecting at least one depolarization wave resulting from the stimulation of the first or other ventricle using an electrode positioned in the orifice of coronary sinus or within a distance of about 20 mm from the orifice of coronary sinus and in coronary sinus; and
   estimating the point in time for detection of the at least one depolarization wave as the point of time for arrival at the AV node.

6. The method of claim 5, further comprising:
    detecting at least one retrograde depolarization wave resulting from the stimulation of the first or other ventricle using the electrode positioned in the orifice of coronary sinus or within a distance of about 20 mm from the orifice of coronary sinus and in coronary sinus;
    estimating the point in time for detection of the at least one retrograde depolarization wave as the point of time for arrival at the AV node;
    comparing the activation time interval difference between the first and second activation time intervals for the depolarization waves resulting from a stimulation of the first and other ventricle, respectively, with an activation time interval difference between the first and second activation time intervals for the retrograde depolarization waves corresponding to the same stimulation in the first and other ventricle; and
    if the activation time intervals differences are substantially equal, determining that the activation time interval difference between the first and second activation time intervals for the depolarization waves was correctly determined.

7. The method according to claim 1, wherein estimating comprises:
    detecting at least one retrograde depolarization wave resulting from the stimulation of the first or other ventricle using an electrode positioned in right or left atrium; and
    estimating the point in time for detection of the at least one depolarization wave as the point of time for arrival at the AV node.

8. The method of claim 7, further comprising:
    distinguishing a subsequent depolarization event due to retrograde conduction from a sinus node induced depolarization by:
        detecting a P-wave interval of the sinus rhythm during a period prior to a determination of first and second activation time intervals; and
        delivering the stimulation to the ventricles using a shorter interval than an P-wave interval of the detected sinus rhythm.

9. A system for determining cardiac pacing therapy of a patient in which an implantable cardiac stimulation device is adapted to be implanted, the system comprising:
    a pacing module configured to provide pacing signals for delivery to the patient via medical leads including electrodes connectable to the pacing module, wherein at least one electrode is adapted to be positioned in each ventricle for activating respective ventricle by delivering stimulation to at least one stimulation site;
    an estimating module configured to estimate a point of time for arrival at the AV node for at least one depolarization wave resulting from a stimulation in a ventricle;
    an activation time interval computing module configured to compute activation time intervals substantially corresponding to the time interval required for at least one depolarization wave to travel from the stimulation site of a ventricle to the AV node using the estimated arrival of the depolarization wave and a point of time for delivery of stimulation; and
    a ventricular pacing controlling module configured to determine a pacing therapy based on an activation time difference between the first and second activation time intervals, wherein the first activation time interval corresponds to the time required for at least one depolarization wave to travel from the stimulation site of the first ventricle to the AV node and the second activation time interval corresponds to the time required for at least one depolarization wave to travel from the stimulation site in the other ventricle to the AV node, the pacing therapy comprising pacing the first ventricle prior to activation of the other ventricle if the activation time difference indicates that the first activation time interval is longer than the second activation time interval and pacing the other ventricle prior to activation of the first ventricle if the activation time difference indicates that the second activation time interval is longer than the first activation time interval.

10. The system of claim 9, further comprising:
    at least one electrode adapted to be positioned in a region in close vicinity to HIS bundle and the valve plane defined by an imaginary approximate half circle below the valve plane having a radius of about 10 mm, the half circle starting at the valve plane on right ventricle side, crossing septum below the valve plane, reaching the valve plane on left ventricle side and ending at the starting point on the right ventricle side; and
    wherein the detecting module is configured to detect at least one depolarization wave resulting from the stimulation of the first or other ventricle using the at least one electrode adapted to be positioned in the region in close vicinity to HIS bundle and the valve plane; and
    wherein the estimating module is configured to use the point of time for detection of the at least one depolarization wave as the point of time for arrival at the AV node in the estimation.

11. The system of claim 9, further comprising:
    at least one electrode adapted to be positioned at a distance between 0-20 mm from HIS bundle and below the valve plane; and
    wherein the detecting module is configured to detect at least one depolarization wave resulting from the stimulation of the first or other ventricle using the at least one electrode adapted to be positioned in the region in close vicinity to HIS bundle and the valve plane; and
    wherein the estimating module is configured to use the point of time for detection of the at least one depolarization wave as the point of time for arrival at the AV node in the estimation.

12. The system of claim 9, further comprising:
    at least one electrode adapted to be positioned in the orifice of coronary sinus or within a distance of about 20 mm from the orifice of coronary sinus within coronary sinus; and
    wherein the detection module is configured to detect at least one depolarization wave resulting from the stimulation of the first or other ventricle using the electrode adapted to be positioned in the orifice of coronary sinus or within a distance of about 20 mm from the orifice of coronary sinus within coronary sinus; and
    wherein the estimation module is configured to use the point of time for detection of the at least one depolarization wave as the point of time for arrival at the AV node in the estimation.

13. The system of claim 12, wherein:
    the detection module is configured to detect at least one retrograde depolarization wave resulting from the stimulation of the first or other ventricle using the electrode adapted to be positioned in the orifice of coronary sinus or within a distance of about 20 mm from the orifice of coronary sinus and in coronary sinus;

the estimation module is configured to estimate the point in time for detection of the at least one retrograde depolarization wave as the point of time for arrival at the AV node; and the activation time interval computing module is configured to:
compare the activation time interval difference between the first and second activation time intervals for the depolarization waves resulting from a stimulation of the first and other ventricle, respectively, with an activation time interval difference between the first and second activation time intervals for the retrograde depolarization waves corresponding to the same stimulation in the first and other ventricle; and
determine that the activation time interval difference between the first and second activation time intervals for the depolarization waves are correct if the activation time intervals differences are substantially equal.

14. The system of claim 9, further comprising:

at least one electrode adapted to be positioned in left or right atrium; and wherein the detection module is configured to detect at least one retrograde depolarization wave resulting from the stimulation of the first or other ventricle using the electrode adapted to be positioned in right or left atrium; and wherein the estimating module is configured to use the point of time for detection of the at least one depolarization wave as the point of time for arrival at the AV node in the estimation.

15. The system of claim 14, wherein:

the detection module is configured to distinguish a subsequent depolarization event due to retrograde conduction from a sinus node induced depolarization by performing a detection of a P-wave interval of the sinus rhythm during a period prior to a determination of first and second activation time intervals; and the pacing module is configured to deliver the stimulation to the ventricles using a shorter interval than an P-wave interval of the detected sinus rhythm.

* * * * *